US011286460B2

(12) United States Patent
Xue et al.

(10) Patent No.: US 11,286,460 B2
(45) Date of Patent: *Mar. 29, 2022

(54) CELL CULTURE MEDIUM FOR EUKARYOTIC CELLS

(71) Applicant: Regeneron Pharmaceuticals, Inc., Tarrytown, NY (US)

(72) Inventors: Wei Xue, Watervliet, NY (US); John Chen, East Greenbush, NY (US); Carolyn Scott, Chesterbrook, PA (US); Theodore Loney, Averill Park, NY (US); Nathaniel Golden, Medfield, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/211,596

(22) Filed: Mar. 24, 2021

(65) Prior Publication Data

US 2021/0261913 A1 Aug. 26, 2021

Related U.S. Application Data

(63) Continuation of application No. 16/752,874, filed on Jan. 27, 2020, now Pat. No. 10,961,500.

(60) Provisional application No. 62/837,263, filed on Apr. 23, 2019.

(51) Int. Cl.
*C12N 5/00* (2006.01)

(52) U.S. Cl.
CPC ......... *C12N 5/0037* (2013.01); *C12N 5/0043* (2013.01); *C07K 2319/30* (2013.01); *C12N 2500/30* (2013.01); *C12N 2500/40* (2013.01); *C12N 2500/46* (2013.01)

(58) Field of Classification Search
CPC ............... C12N 5/0037; C12N 5/0043; C12N 2500/30; C12N 2500/46; C12N 2500/40; C07K 2319/30
See application file for complete search history.

(56) References Cited

U.S. PATENT DOCUMENTS

| | | | |
|---|---|---|---|
| 6,927,004 B2 | 8/2005 | Eurlings et al. | |
| 7,087,411 B2 | 8/2006 | Daly et al. | |
| 7,279,159 B2 | 10/2007 | Daly et al. | |
| 2003/0096414 A1* | 5/2003 | Ciccarone | C12N 5/0043 435/383 |
| 2006/0148074 A1 | 7/2006 | Gorfien et al. | |
| 2012/0035110 A1* | 2/2012 | Grillberger | A61P 29/00 514/14.1 |
| 2018/0223249 A1 | 8/2018 | Johsnson et al. | |

FOREIGN PATENT DOCUMENTS

| | | |
|---|---|---|
| EP | 3 431 588 A1 | 1/2019 |
| WO | WO1989004867 A1 | 6/1989 |
| WO | WO 2017/024062 A1 | 2/2017 |

OTHER PUBLICATIONS

Raina et al. Inhibition of the synthesis of polyamines and macromolecules by 5'-methylthioadenosine and 5'-alkylthiotubercidins in BHK21 cells. Biochem. J. (1982) 204, 697-703 (Year: 1982).*
Dawn M. Ecker, Susan Dana Jones & Howard L. Levine, The therapeutic monoclonal antibody market, 7 MABS 9-14 (2014).
Brian A. Baldo, Chimeric Fusion binding molecules Used for Therapy: Indications, Mechanisms, and Safety, 38 Drug Safety 455-479 (2015).
Darius Ghaderi et al., Production platforms for biotherapeutic glycoproteins. Occurrence, impact, and challenges of non-human sialylation, 28 Biotechnology and Genetic Engineering Reviews 147-176 (2012).
A. Ashkenazi et al., Protection against endotoxic shock by a tumor necrosis factor receptor immunoadhesin., 88 Proceedings of the National Academy of Sciences 10535-10539 (1991).
Randal A. Byrn et al., Biological properties of a CD4 immunoadhesin, 344 NATURE 667-670 (1990).
Li et al. Feeding Lactate for CHO Cell Culture Processes: Impact on Culture Metabolism and Performance. Biotechnol. Bioeng. 2012;109: 1173-1186. (Year: 2012).
Bavarese Todd M. et al: "Conversion of 5'-Deoxy-5'-methylthioadenosine and 5'-Deoxy-5'- methylthioinosine to Methionine in Cultured Human Leukemic Cells 1," Cancer Research Williams General Hospital, Biochemical Pharmacology, Oct. 1, 1983, pp. 4699-4702 retrieved from the internet: URL"https"//cancerres.aacrjournals.org.
International Search Report Application No. PCT/2020/029370, Filing Date Apr. 22, 2020, dated Jul. 2, 2020.

* cited by examiner

*Primary Examiner* — Taeyoon Kim
(74) *Attorney, Agent, or Firm* — Kramer Levin Naftalis & Frankel LLP; Stephen J. Gaudet

(57) ABSTRACT

Cell culture media are provided herein as are methods of using the media for cell culture and protein production from cells.

7 Claims, 6 Drawing Sheets

CELL CULTURE MEDIUM FOR EUKARYOTIC CELLS

FIELD

The present invention generally pertains to a cell culture medium for eukaryotic cells and the production of natural and recombinant products derived therefrom.

BACKGROUND

Cell culture manufacturing technology is widely used for the production of biopharmaceuticals. As the demand for biopharmaceuticals increase, demand for increase in cell growth, viability and protein production have also increased considerably. Much effort is now being placed on methods and strategies for growing, feeding, and maintaining cell cultures.

New cell culture methods that provide even incremental improvements in recombinant protein production are valuable, given the challenges and expense of large scale cell culture processes and the growing demand for greater quantities of and lower costs for biological products. Improvements to cell culture processes, recombinant polypeptide expression, titer, and cell viability that can lead to higher production levels, thereby reducing the costs associated with manufacturing protein therapeutics are needed.

SUMMARY

Growth in the development, manufacture and sale of protein-based biopharmaceutical products has led to an increasing demand for production methods that can improve production of the biopharmaceutical products.

Embodiments disclosed herein address the aforementioned demands by providing methods and media for manufacture of such biopharmaceutical products.

The disclosure, at least in part, provides a cell culture medium for eukaryotic cells.

In one exemplary embodiment, the cell culture medium for eukaryotic cells can comprise a basal medium. In one aspect of this embodiment, the cell culture medium can further comprise 5-methylthioadenosine. In another aspect of this embodiment, the cell culture medium can comprise at least about 10 nM of 5-methythioadenosine. In yet another aspect of this embodiment, the cell culture medium can comprise about 10 nM to about 200 nM of 5-methythioadenosine. In one aspect of this embodiment, the cell culture medium can further comprise nicotinamide. In another aspect of this embodiment, the cell culture medium can comprise at least about 50 nM of nicotinamide. In yet another aspect of this embodiment, the cell culture medium can comprise about 2000 nM of 5-nicotinamide. In one aspect of this embodiment, a titer of a protein grown in the cell culture medium is at least about 2% greater than another cell culture medium not comprising at least about 10 nM 5-methylthioadenosine. In another aspect of this embodiment, a titer of a protein grown in the cell culture medium is at least about 2% greater than another cell culture medium not comprising at least about 50 nM nicotinamide. In one aspect of this embodiment, the cell culture medium can optionally further comprise one or more acids selected from lactic acid, phenyl lactic acid, indolelactic acid, succinic acid, alpha-hydroxyisovaleric acid, alpha-hydroxyisocaproic acid, 2-(4-hydroxy-phenyl)lactic acid, or 2-hydroxy-3-methylvaleric acid, salts of these acids, esters of these acids and combinations thereof. In one aspect of this embodiment, the cell culture medium can optionally further comprise sugars, amino acids, vitamins, salts, trace metal ions, purines, and/or pyrimidines. In one aspect of this embodiment, the cell culture medium can comprise salts or esters of 5-methythioadenosine. In another aspect of this embodiment, the cell culture medium can comprise salts or esters of nicotinamide. In one aspect of this embodiment, the cell culture medium can have a pH of about 6.5 to about 8. In one aspect of this embodiment, the cell culture medium does not have a protein derived from an animal. In one aspect of this embodiment, the cell culture medium can be a serum-free medium. In one aspect of this embodiment, the cell culture medium can be a chemically-defined medium.

In one exemplary embodiment, the cell culture medium for eukaryotic cells can comprise a feed medium. In one aspect of this embodiment, the cell culture medium can further comprise 5-methylthioadenosine. In another aspect of this embodiment, the cell culture medium can comprise at least about 10 nM of 5-methythioadenosine. In yet another aspect of this embodiment, the cell culture medium can comprise about 10 nM to about 200 nM of 5-methythioadenosine. In one aspect of this embodiment, the cell culture medium can further comprise nicotinamide. In another aspect of this embodiment, the cell culture medium can comprise at least about 50 nM of nicotinamide. In yet another aspect of this embodiment, the cell culture medium can comprise about 50 nM to about 2000 nM of 5-nicotinamide. In an alternate aspect of this embodiment, the cell culture medium can further comprise 5-methylthioadenosine and nicotinamide. In one aspect of this embodiment, the cell culture medium can optionally further comprise one or more acids selected from lactic acid, phenyl lactic acid, indolelactic acid, succinic acid, alpha-hydroxyisovaleric acid, alpha-hydroxyisocaproic acid, 2-(4-hydroxy-phenyl)lactic acid, or 2-hydroxy-3-methylvaleric acid, salts of these acids, esters of these acids and combinations thereof. In one aspect of this embodiment, the cell culture medium can optionally further comprise sugars, amino acids, vitamins, salts, trace metal ions, purines, and/or pyrimidines. In one aspect of this embodiment, the cell culture medium can comprise salts or esters of 5-methythioadenosine. In another aspect of this embodiment, the cell culture medium can comprise salts or esters of nicotinamide. In one aspect of this embodiment, the cell culture medium can have a pH of about 6.5 to about 8. In one aspect of this embodiment, the cell culture medium does not have a protein derived from an animal. In one aspect of this embodiment, the cell culture medium can be a serum-free medium. In one aspect of this embodiment, the cell culture medium can be a chemically-defined medium. In one aspect of this embodiment, the cell culture medium can optionally comprise nicotinamide. In one aspect of this embodiment, a titer of a protein grown in the cell culture medium is at least about 2% greater than another cell culture medium not comprising at least about 10 nM 5-methylthioadenosine. In another aspect of this embodiment, a titer of a protein grown in the cell culture medium is at least about 2% greater than another cell culture medium not comprising at least about 50 nM nicotinamide.

The disclosure, at least in part, provides a method of producing a protein.

In one exemplary embodiment, the method of producing a protein can comprise culturing eukaryotic cells having a nucleic acid encoding the protein in a cell culture production medium and feeding the eukaryotic cells using an enriched media having 5-methylthioadenosine during a time period. In one aspect of this embodiment, the enriched media can have at least about 1 nM 5-methylthioadenosine. In one aspect of this embodiment, the cell culture production medium can comprise one or more acids selected from lactic acid, phenyl lactic acid, indolelactic acid, succinic acid, alpha-hydroxyisovaleric acid, alpha-hydroxyisocaproic acid, 2-(4-hydroxy-phenyl)lactic acid, or 2-hydroxy-3-methylvaleric acid, salts of these acids, esters of these acids and combinations thereof. In one aspect of this embodiment, the cell culture production medium can comprise sugars, amino acids, vitamins, salts, trace metal ions, purines, and/or pyrimidines. In one aspect of this embodiment, the cell culture production medium can comprise salts or esters of 5-methythioadenosine. In one aspect of this embodiment, the cell culture production medium can have a pH of about 6.5 to about 8. In one aspect of this embodiment, the cell culture production medium does not have a protein derived from an animal. In one aspect of this embodiment, the cell culture production medium can be a serum-free medium. In one aspect of this embodiment, the cell culture production medium can be a chemically-defined medium. In one aspect of this embodiment, the eukaryotic cells can be selected from Baby Hamster Kidney cell lines, Chinese Hamster Ovary cell lines, Murine myeloma cell lines, Mouse myeloma cell lines, Human embryonic kidney cell lines, Human-retina-derived cell lines, and/or Amniocyte cell lines. In one aspect of this embodiment, the protein can be selected from the group consisting of an antibody or a fragment or derivative thereof, a fusion protein, and a physiologically active non-antibody protein. In one aspect of this embodiment, the method can produce a titer of a protein at least about 2% greater than a titer of a protein in a cell culture production medium not having at least about 10 nM 5-methythioadenosine. In one aspect of this embodiment, the enriched media can optionally comprise nicotinamide. In one aspect of this embodiment, the method of producing a protein can be a fed-batch method.

In one exemplary embodiment, the method of producing a protein can comprise culturing eukaryotic cells having a nucleic acid encoding the protein in a cell culture production medium and feeding the eukaryotic cells using an enriched media having nicotinamide during a certain time period. In one aspect of this embodiment, the enriched media can have at least about 5 nM nicotinamide. In one aspect of this embodiment, the cell culture production medium can comprise one or more acids selected from lactic acid, phenyl lactic acid, indolelactic acid, succinic acid, alpha-hydroxy-isovaleric acid, alpha-hydroxyisocaproic acid, 2-(4-hydroxy-phenyl)lactic acid, or 2-hydroxy-3-methylvaleric acid, salts of these acids, esters of these acids and combinations thereof. In one aspect of this embodiment, the cell culture production medium can comprise sugars, amino acids, vitamins, salts, trace metal ions, purines, and/or pyrimidines. In one aspect of this embodiment, the cell culture production medium can comprise salts or esters of nicotinamide. In one aspect of this embodiment, the cell culture production medium can have a pH of about 6.5 to about 8. In one aspect of this embodiment, the cell culture production medium does not have a protein derived from an animal. In one aspect of this embodiment, the cell culture production medium can be a serum-free medium. In one aspect of this embodiment, the cell culture production medium can be a chemically-defined medium. In one aspect of this embodiment, the eukaryotic cells can be selected from Baby Hamster Kidney cell lines, Chinese Hamster Ovary cell lines, Murine myeloma cell lines, Mouse myeloma cell lines, Human embryonic kidney cell lines, Human-retina-derived cell lines, and/or Amniocyte cell lines. In one aspect of this embodiment, the protein can be selected from the group consisting of an antibody or a fragment or derivative thereof, a fusion protein, and a physiologically active non-antibody protein. In one aspect of this embodiment, the method can produce a titer of a protein at least about 2% greater than a titer of a protein in a cell culture production medium not having at least about 50 nM nicotinamide. In one aspect of this embodiment, the enriched media can optionally comprise 5-methylthioadenosine. In one aspect of this embodiment, the method of producing a protein can be a fed-batch method.

The disclosure, at least in part, provides a method for increasing production of a protein.

In one exemplary embodiment, the method for increasing production of a protein can comprise culturing eukaryotic cells in a cell culture medium, supplementing the cell culture medium with 5-methythioadenosine, and expressing a protein. In one aspect of this embodiment, concentration of 5-methythioadenosine can be at least about 10 nM. In one aspect of this embodiment, concentration of 5-methythioadenosine can be about 10 nM to about 200 nM. In one aspect of this embodiment, the cell culture medium can comprise one or more acids selected from lactic acid, phenyl lactic acid, indolelactic acid, succinic acid, alpha-hydroxyisovaleric acid, alpha-hydroxyisocaproic acid, 2-(4-hydroxyphenyl)lactic acid, or 2-hydroxy-3-methylvaleric acid, salts of these acids, esters of these acids and combinations thereof. In one aspect of this embodiment, the cell culture medium can comprise sugars, amino acids, vitamins, salts, trace metal ions, purines, and/or pyrimidines. In one aspect of this embodiment, the cell culture medium can comprise salts or esters of 5-methythioadenosine. In one aspect of this embodiment, the cell culture medium can have a pH of about 6.5 to about 8. In one aspect of this embodiment, the cell culture medium does not have a protein derived from an animal. In one aspect of this embodiment, the cell culture medium can be a serum-free medium. In one aspect of this embodiment, the cell culture medium can be a chemically-defined medium. In one aspect of this embodiment, eukaryotic cells can be selected from Baby Hamster Kidney cell lines, Chinese Hamster Ovary cell lines, Murine myeloma cell lines, Mouse myeloma cell lines, Human embryonic kidney cell lines, Human-retina-derived cell lines, and/or Amniocyte cell lines. In one aspect of this embodiment, the protein can be selected from the group consisting of an antibody or a fragment or derivative thereof, a fusion protein, and a physiologically active non-antibody protein. In one aspect of this embodiment, the supplementation with 5-methythioadenosine increases titer of the recombinant protein by at least about 2%. In one aspect of this embodiment, the cell culture medium can be optionally supplemented with nicotinamide.

In one exemplary embodiment, the method for increasing production of a protein can comprise culturing eukaryotic cells in a cell culture medium, supplementing the cell culture medium with nicotinamide, and expressing a protein. In one aspect of this embodiment, concentration of nicotinamide can be at least about 50 nM. In one aspect of this embodiment, concentration of 5-methythioadenosine can be about 50 nM to about 2000 nM. In one aspect of this embodiment, the cell culture medium can comprise one or more acids selected from lactic acid, phenyl lactic acid, indolelactic acid, succinic acid, alpha-hydroxyisovaleric acid, alpha-hydroxyisocaproic acid, 2-(4-hydroxyphenyl)lactic acid, or 2-hydroxy-3-methylvaleric acid, salts of these acids, esters of these acids and combinations thereof. In one aspect of this embodiment, the cell culture medium can comprise sugars, amino acids, vitamins, salts, trace metal ions, purines, and/or pyrimidines. In one aspect of this embodiment, the cell culture medium can comprise salts or esters of nicotinamide. In one aspect of this embodiment, the cell culture medium can have a pH of about 6.5 to about 8. In one aspect of this embodiment, the cell culture medium does not have a protein derived from an animal. In one aspect of this embodiment, the cell culture medium can be a serum-free medium. In one aspect of this embodiment, the cell culture medium can be a chemically-defined medium. In one aspect of this embodiment, eukaryotic cells can be selected from Baby Hamster Kidney cell lines, Chinese Hamster Ovary cell lines, Murine myeloma cell lines, Mouse myeloma cell lines, Human embryonic kidney cell lines, Human-retina-derived cell lines, and/or Amniocyte cell lines. In one aspect of this embodiment, the protein can be selected from the group consisting of an antibody or a fragment or derivative thereof, a fusion protein, and a physiologically active non-antibody protein. In one aspect of this embodiment, the supplementation with nicotinamide increases titer of the recombinant protein by at least about 2%. In one aspect of this embodiment, the cell culture medium can be optionally supplemented with 5-methyladenosine.

The disclosure, at least in part, provides a method for producing a protein.

In one exemplary embodiment, the method for producing a protein can comprise introducing into cell(s) a nucleic acid comprising a sequence encoding a protein and culturing the cell(s) in a cell culture medium. In one aspect of this embodiment, the cell culture medium can be enriched with at least about 10 nM 5-methythioadenosine. In another aspect of this embodiment, the cell culture medium can be enriched with at least about 50 nM nicotinamide. In yet another aspect of this embodiment, the cell culture medium can be enriched with at least about 10 nM 5-methythioadenosine and at least about 50 nM nicotinamide. In one aspect of this embodiment, the method for producing a protein can further comprise maintaining the cell culture medium to express a higher titer of protein in the cell(s). In one aspect of this embodiment, the method for producing a protein can further comprise harvesting the protein. In one aspect of this embodiment, the cell(s) can be selected from Baby Hamster Kidney cell lines, Chinese Hamster Ovary cell lines, Murine myeloma cell lines, Mouse myeloma cell lines, Human embryonic kidney cell lines, Human-retina-derived cell lines, and/or Amniocyte cell lines. In one aspect of this embodiment, the cell culture medium can further comprise one or more acids selected from lactic acid, phenyl lactic acid, indolelactic acid, succinic acid, alpha-hydroxyisovaleric acid, alpha-hydroxyisocaproic acid, 2-(4-hydroxyphenyl)lactic acid, or 2-hydroxy-3-methylvaleric acid, salts of these acids, esters of these acids and combinations thereof. In one aspect of this embodiment, the cell culture medium can further comprise sugars, amino acids, vitamins, salts, trace metal ions, purines, and/or pyrimidines. In one aspect of this embodiment, the cell culture medium can have a pH of about 6.5 to about 8. In one aspect of this embodiment, the cell culture medium does not have a protein derived from an animal. In one aspect of this embodiment, the cell culture medium can be a serum-free medium. In one aspect of this embodiment, the cell culture medium can be a chemically-defined medium. In one aspect of this embodiment, the protein can be selected from the group consisting of an antibody or a fragment or derivative thereof, a fusion protein, and a physiologically active non-antibody protein. In one aspect of this embodiment, the method can express a 2% higher titer of protein in the cell(s) compared to cell(s) grown in a cell culture medium that does not have at least about 10 nM 5-methythioadenosine. In another aspect of this embodiment, the method for producing a protein can further comprise maintaining the cell culture medium to express a 2% higher titer of protein in the cell(s) compared to cell(s) grown in a cell culture medium that does not have at least about 50 nM nicotinamide.

DETAILED DESCRIPTION

Figure 1:
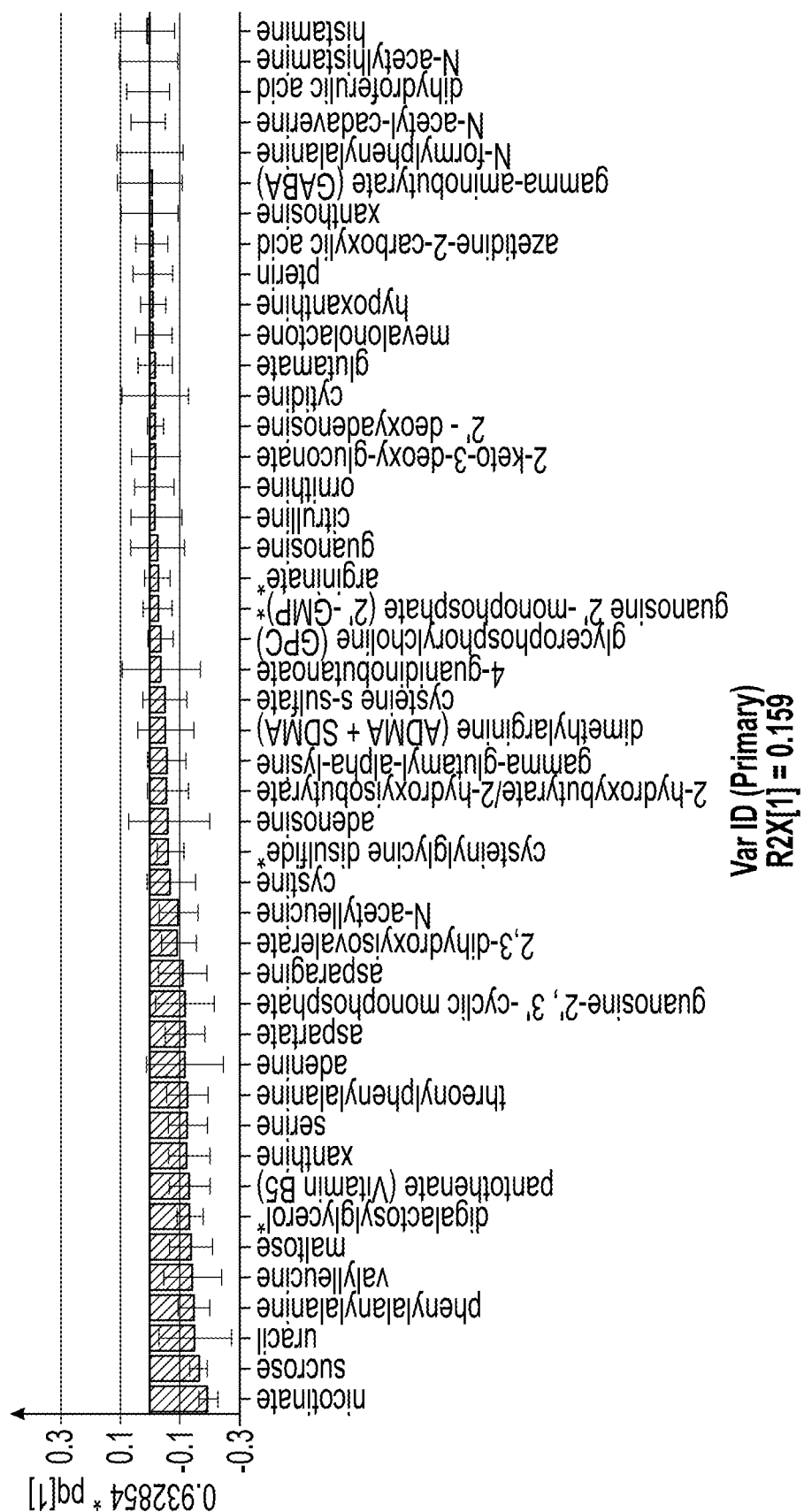
FIG. 1 shows the multivariate analysis (MVA) result of investigation of components present in soy hydrolysate.
Figure 1:
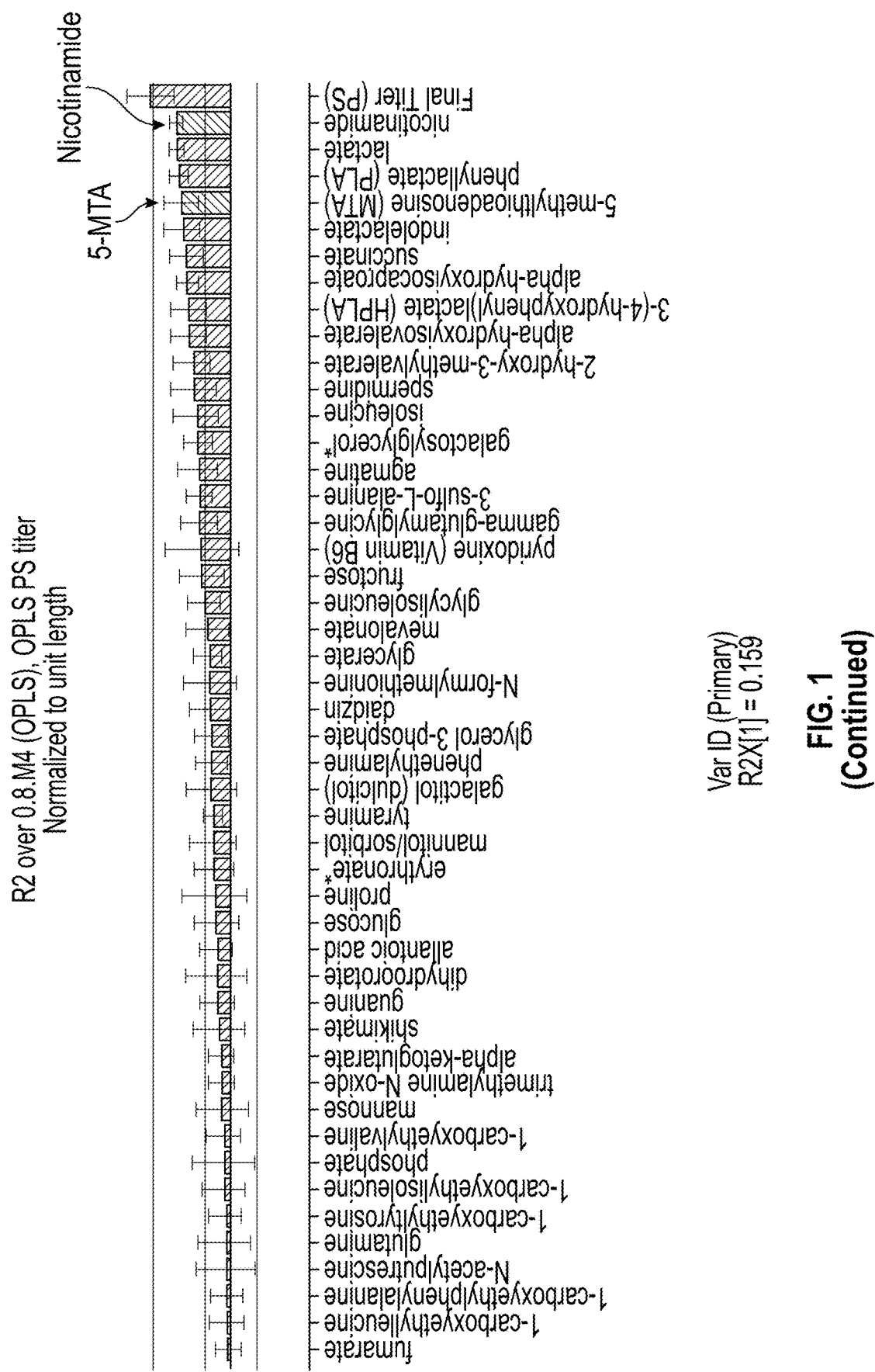
Figure 2:
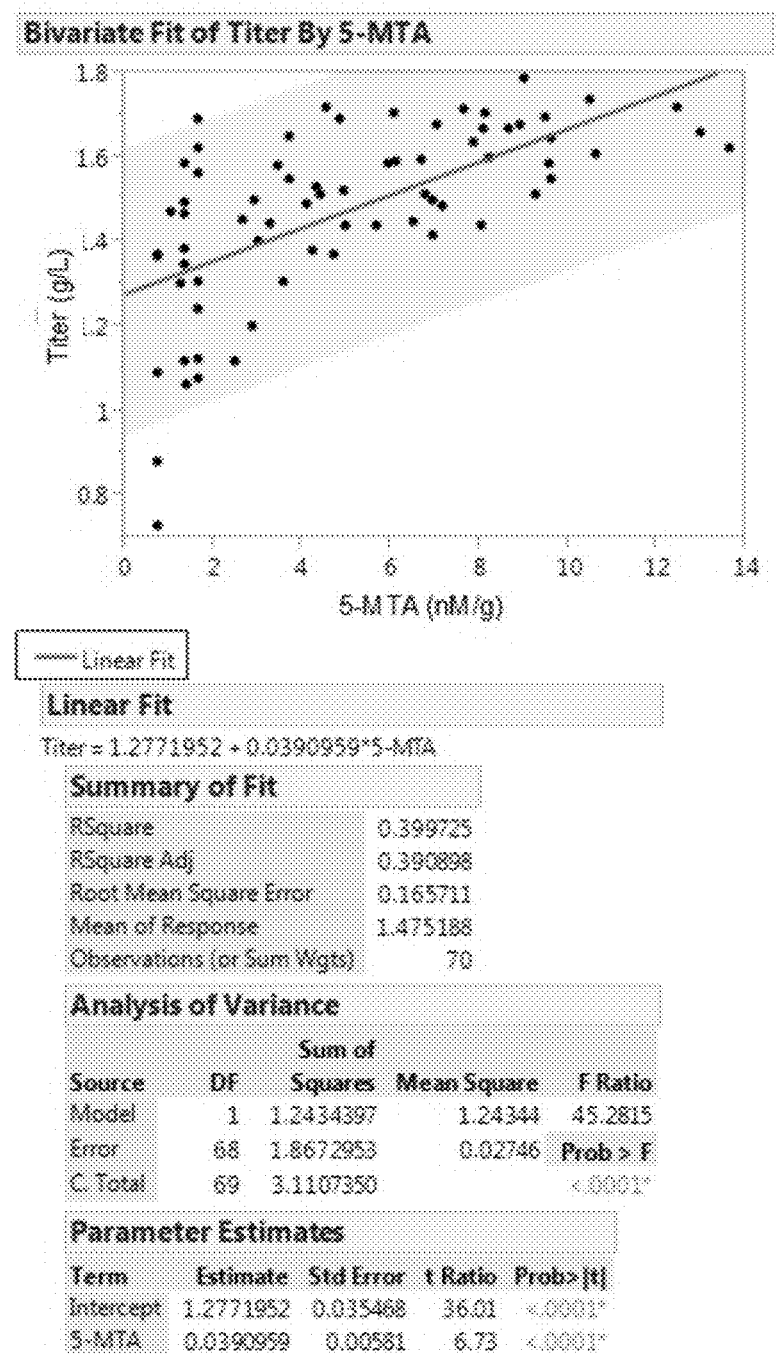
FIG. 2 shows correlation data obtained from studying the effect of 5-methythioadenosine concentration in an enriched medium used to supplement a cell culture medium to the protein titer (g/L) according to one exemplary embodiment.
Figure 3:
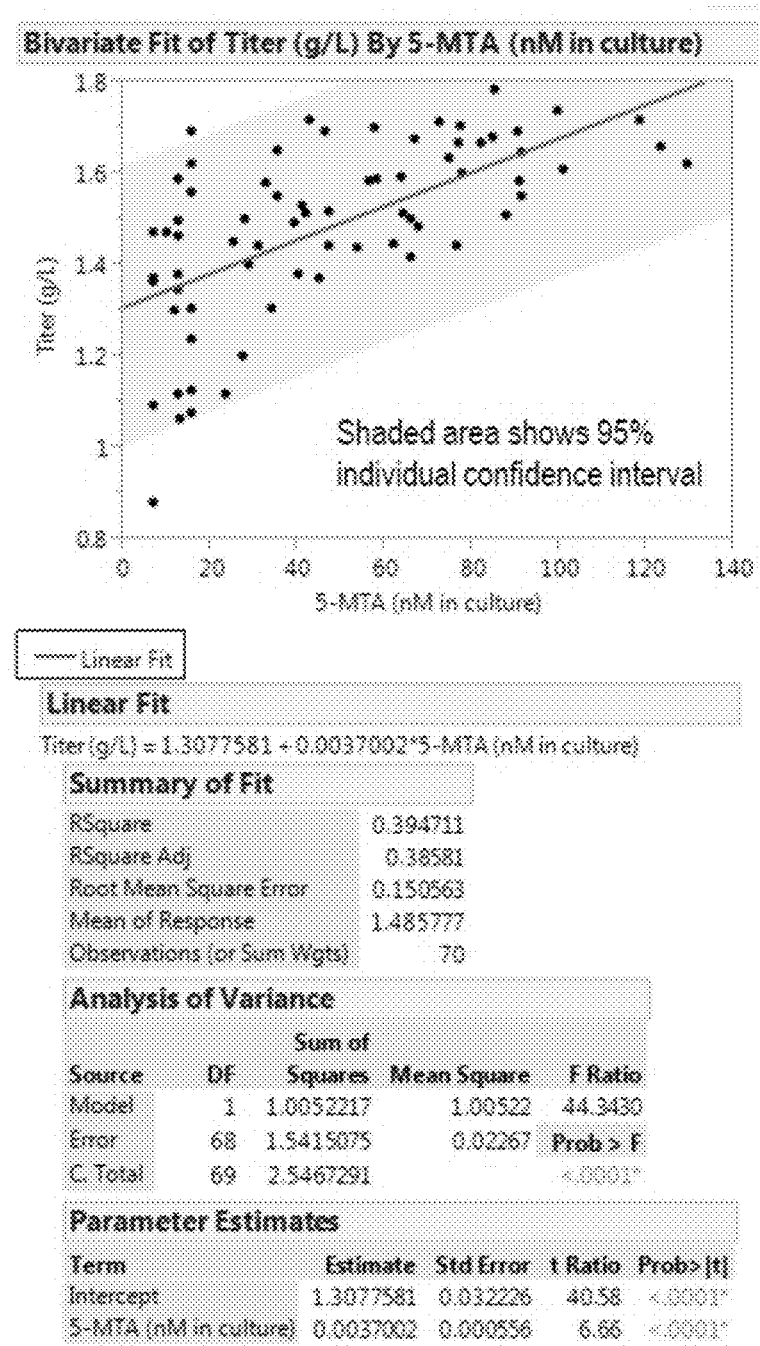
FIG. 3 shows a regression line relating to the variables (N=70) used to evaluate the effect of concentration of 5-methythioadenosine in a cell culture medium to the protein titer (g/L) according to one exemplary embodiment.
Figure 4:
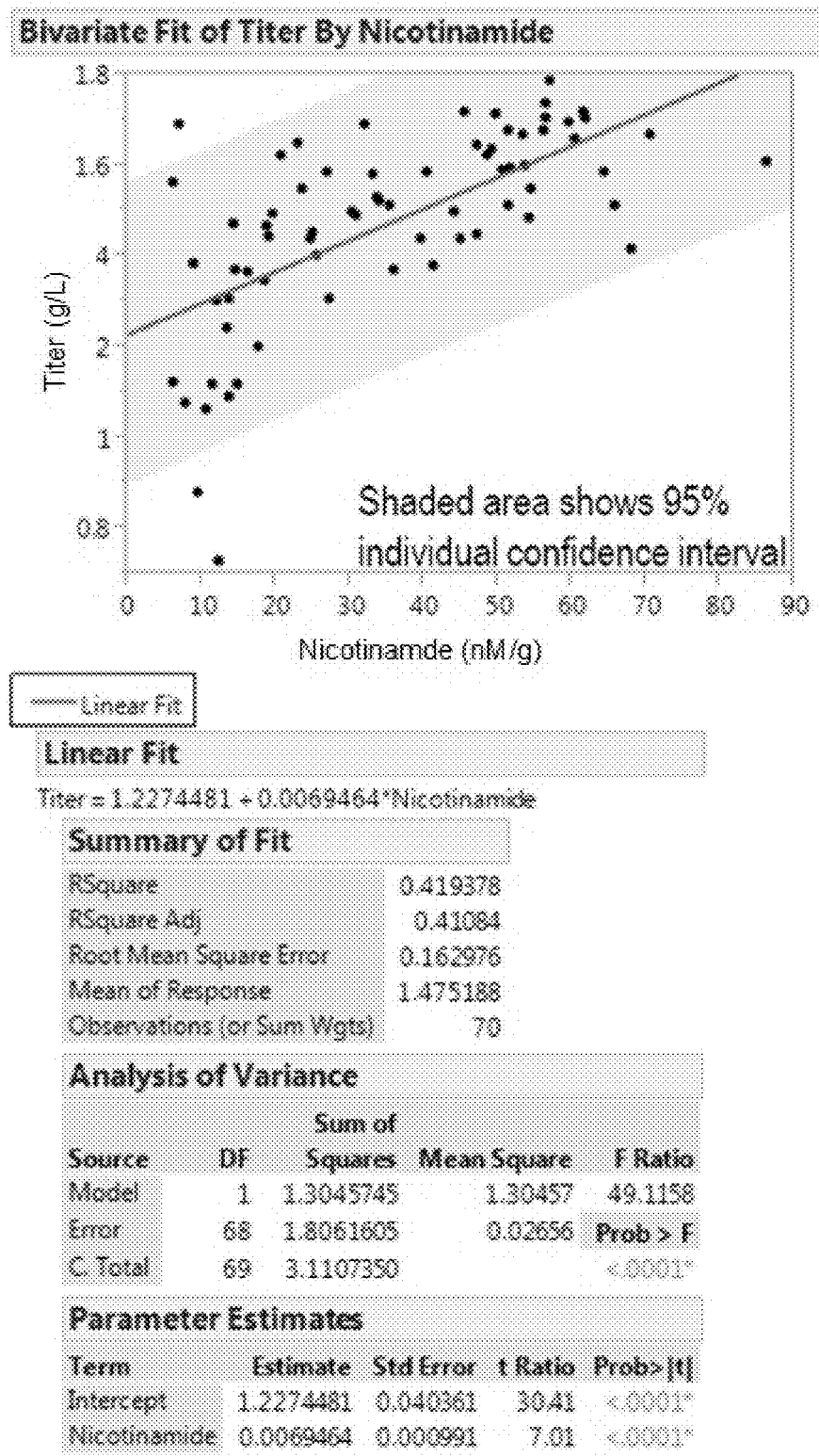
FIG. 4 shows correlation data obtained from studying the effect of nicotinamide concentration in an enriched medium used to supplement a cell culture medium to the protein titer (g/L) according to one exemplary embodiment.
Figure 5:
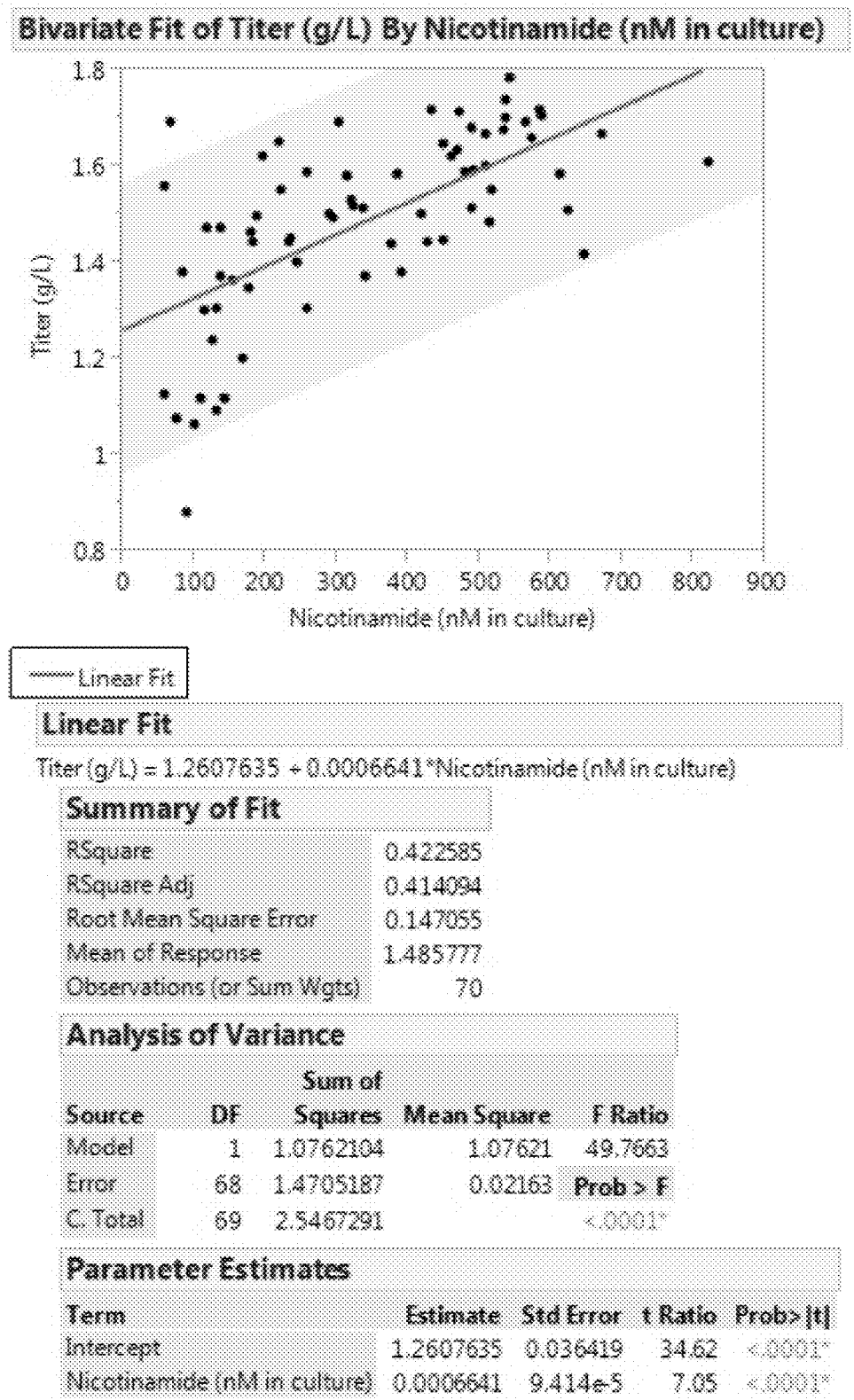
FIG. 5 shows a regression line relating to the variables (N=70) used to evaluate the effect of concentration of nicotinamide in a cell culture medium to the protein titer (g/L) according to one exemplary embodiment.

Biopharmaceutical products have been very effective in diagnostic and therapeutic applications (Dawn M Ecker, Susan Dana Jones & Howard L Levine, *The therapeutic monoclonal antibody market*, 7 mAbs 9-14 (2014); Brian A. Baldo, *Chimeric Fusion binding molecules Used for Therapy: Indications, Mechanisms, and Safety*, 38 Drug Safety 455-479 (2015)). Some cell culture media used for culturing cells to produce biopharmaceutical products have been well documented in the literature and a number of media are commercially available. Typical components of cell culture media include amino acids, organic and inorganic salts, vitamins, trace metals, sugars, lipids and nucleic acids, the types and amounts of which may vary depending upon the particular requirements of a given cell or tissue type.

One goal of protein production can be optimization of cell culture in order to obtain the greatest amount of protein and the most efficient means of productivity. Any improvement, including incremental improvements, can have enormous benefits economically. In the pharmaceutical industry, optimization of protein production for biologics used in therapies for the treatment of disease is advantageous, as any improvement can have significant impact when the biologic is manufactured on a large scale. As such, there remains a need to maximize protein production from cell cultures expressing biologic proteins for use in medicine.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure provides a method for producing a protein.

As used herein, the term "protein" includes any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion binding molecules, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Recombinant proteins may be produced using recombinant cell-based production systems, such as the insect baculovirus system, yeast systems (e.g., *Pichia* sp.), mammalian systems (e.g., CHO cells and CHO derivatives like CHO-K1 cells). For a recent review discussing bio-therapeutic proteins and their production, see Darius Ghaderi et al., *Production platforms for biotherapeutic glycoproteins. Occurrence, impact, and challenges of non-human sialylation*, 28 BIOTECHNOLOGY AND GENETIC ENGINEERING REVIEWS 147-176 (2012). In some embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein or the protein or the recombinant protein or the recombinant protein can be an antibody, a bispecific antibody, a multispecific antibody, antibody fragment, a monoclonal antibody, a Fc-fusion binding molecule, a F(ab')2 fragment, a Fc fragment, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ can be composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

As used herein, the term "fusion protein" or "Fc fusion protein" comprise part or all of two or more proteins, one of which can be an Fc portion of an immunoglobulin molecule, that are not fused in their natural state. Preparation of fusion protein can comprise certain heterologous polypeptides fused to various portions of antibody-derived polypeptides (including the Fc domain) has been described, e.g., by A. Ashkenazi et al., *Protection against endotoxic shock by a tumor necrosis factor receptor immunoadhesin.*, 88 Proceedings of the National Academy of Sciences 10535-10539 (1991); Randal A. Byrn et al., *Biological properties of a CD4 immunoadhesin,* 344 Nature 667-670 (1990); Diane Hollenbaugh & Alejandro Aruffo, Construction of Immunoglobulin Fusion binding molecules, Current Protocols in Immunology (2002). "Receptor Fc fusion protein" comprise one or more of one or more extracellular domain(s) of a receptor coupled to an Fc moiety, which in some embodiments can comprise a hinge region followed by a $C_H2$ and $C_H3$ domain of an immunoglobulin. In some embodiments, the Fc-fusion protein can contain two or more distinct receptor chains that bind to a single or more than one ligand(s). For example, an Fc-fusion protein can be a trap, such as for example an IL-1 trap (e.g., Rilonacept, which contains the IL-1 RAcP ligand binding region fused to the IL-1R1 extracellular region fused to Fc of hIgG1; see U.S. Pat. No. 6,927,004, which is herein incorporated by reference in its entirety), or a VEGF Trap (e.g., Aflibercept, which contains the Ig domain 2 of the VEGF receptor Flt1 fused to the Ig domain 3 of the VEGF receptor Flk1 fused to Fc of hIgG1; e.g., see U.S. Pat. Nos. 7,087,411 and 7,279,159, which are herein incorporated by reference in their entirety. Aflibercept is secreted into the culture medium during expression.).

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

In some exemplary embodiments, the protein or the protein or the recombinant protein or the recombinant protein can be an antibody variant or a binding molecule variant.

"Variant" or "binding molecule variant" as used herein can include a binding molecule that differs from a target binding molecule by virtue of at least one amino acid modification or a post-translational modification. The variant may refer to the binding molecule itself, a composition comprising the binding molecule, or the amino sequence that encodes it. Preferably, the binding molecule variant has at least one amino acid modification compared to the parent binding molecule, e.g., from about one to about ten amino acid modifications, and preferably from about one to about five amino acid modifications compared to the parent. The binding molecule variant sequence herein will preferably possess at least about 80% homology with a parent binding molecule sequence, and more preferably at least about 90% homology, most preferably at least about 92% homology.

In some exemplary embodiments, the protein or the protein or the recombinant protein or the recombinant protein can be a protein with a specific post-translational modification.

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (e.g., signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g., methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (e.g., the conversion of arginine to citrulline by deimination), and deamidation (e.g., the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See http://www.uniprot.org/docs/ptmlist for a more detailed controlled vocabulary of PTMs curated by UniProt.

In some exemplary embodiments, the disclosure provides a cell culture medium for eukaryotic cells comprising a basal medium or a feed medium and 5-methylthioadenosine and/or nicotinamide.

As used herein, the term "cell culture medium" refers to cells grown in an artificial (e.g., an in vitro) environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture." Suitable culture conditions for eukaryotic cells can be found in the art e.g. Animal cell culture: A Practical Approach, D. Rickwood, ed., Oxford University Press, New York (1992). Cell culture medium may be optimized for a specific cell culture use, including, for example, cell culture growth medium which can be formulated to promote cellular growth, or cell culture production medium which can be formulated to promote recombinant protein production. The terms nutrient, ingredient, and component are used interchangeably herein to refer to the constituents that make up a cell culture medium.

As used herein, the term "basal medium" can refer to any medium which can be capable of supporting growth of cells. The basal medium can comprise a number of ingredients, including amino acids, vitamins, organic and inorganic salts, sources of carbohydrate, each ingredient being present in an amount which supports the cultivation of a cell in vitro. The medium may contain auxiliary substances, such as buffer substances like sodium bicarbonate, oxidation stabilizers, stabilizers to counteract mechanical stress, or protease inhibitors. Examples of basal media include, but are not limited to, Dulbecco's Modified Eagle's Medium (DMEM), DME/F12, Minimal Essential Medium (MEM), Basal Medium Eagle (BME), Medium 199, RPMI 1640, F-10, F-12, α-Minimal Essential Medium (α-MEM), Glasgow's Minimal Essential Medium (G-MEM), PF CHO (SAFC Biosciences), Iscove's Modified Dulbecco's Medium or combinations thereof, and others that are known from the literature or are commercially available.

As used herein, the term "feed medium" includes a medium containing one or more nutrients that can be added to the culture beginning at some time after inoculation. The feed medium can also be a combination feed comprising a basal medium and at least one type of hydrolysate, e.g., soy-based, hydrolysate, a yeast-based hydrolysate, or a combination of the two types of hydrolysates. Further, the feed medium can also include only a basal medium, such as a concentrated basal medium, or may include only hydrolysates, or concentrated hydrolysates.

As used herein, the term "eukaryotic cells" can include individual cells, tissues, organs, insect cells, avian cells, mammalian cells, primary cells, continuous cell lines, stem cells and/or genetically engineered cells, such as recombinant cells expressing a heterologous polypeptide or protein. Some mammalian cells suitable for cultivation in the cell culture medium can be of human origin or non-human origin can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPMI2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

As used herein, "nicotinamide" can also be referred to as niacinamide, Nicotinic acid amide, Pyridine-3-carboxylic acid amide, Vitamin B3, Vitamin PP, 3-Pyridinecarboxamide, CAS number 98-92-0, or $C_6H_6N_2O$.

As used herein, "5-methylthioadenosine" can also be referred to as 5-Deoxy-5'-methylthioadenosine, CAS number 2457-80-9, $C_{11}H_{15}N_5O_3S$, MTA, MeSAdo, NSC 335422, Vitamin L2, salts of 5-methylthioadenosine, or esters of 5-methylthioadenosine. Non-limiting examples of salts suitable for 5-methylthioadenosine, for example, include acid addition salts. The acid addition salts may be inorganic and organic acid addition salts, e.g., hydrochlorides, sulfates, nitrates, carbonates, phosphates, formates, oxalates, citrates, ascorbic acid, methanesulfonic acid, 1,4-butane sulfonate, 1,5-pentane sulfonate and p-toluenesulphonate salts.

In some exemplary embodiments, the disclosure provides a method of producing a protein comprising culturing eukaryotic cells having a nucleic acid encoding the protein in a cell culture production medium.

Cell culture medium or cell culture production medium can be supplemented with enriched media containing components, such as nutrients and amino acids, which are consumed during the course of the production phase of the cell culture.

As used herein, the term "cell culture production medium" can include a cell culture medium designed to be used during the production phase of a cell culture.

In some exemplary embodiments, the cell culture production medium or the cell culture medium can be a serum-free medium.

As used herein, the term "serum-free medium" includes a cell culture medium that does not contain animal serum, such as fetal bovine serum. Serum-free media may or may not contain hydrolysates, growth factors, hormones, carrier proteins, and attachment factors. Examples of known serum-free medium include CHO—S-SFM II (Gibco) and 293 SFM II (Gibco).

In some exemplary embodiments, the cell culture production medium or the cell culture medium can be a medium with no animal-derived protein.

As used herein, the term "medium with no animal-derived protein" can refer to a medium that does not contain proteins and protein components from higher multicellular non-plant eukaryotes (that is, vertebrates), that possess the secondary, tertiary and quaternary structures characteristic of the proteins as they occur in nature. Such a medium does not contain proteins, such as albumin, transferrin, insulin and other growth factors. However, animal-derived proteins and protein components are different from non-animal proteins, small polypeptides and oligopeptides obtainable from plants (usually about 10-30 amino acids in length), such as the soy bean, and lower eukaryotes, such as yeast. On contacting or inoculating the cells with an animal-derive protein medium, the medium will contain animal proteins shed or secreted by those cells, including any recombinant proteins expressed by genetically modified cells if such cells are cultivated. Thus, the term animal protein free medium, and biological materials and preparations produced therewith, is not to be construed to require the absence of proteins shed or secreted by cells propagated in the media, but rather refers to a lack of direct supplementation of media with animal proteins and protein components obtained from animal sources or the like produced recombinantly.

In some exemplary embodiments, the cell culture production medium or the cell culture medium can be a chemically-defined medium.

As used herein, a "chemically-defined medium" can include a medium composed of pure ingredients in measured concentrations. A chemically-defined medium can contain a simple sugar as the carbon and energy source, an inorganic nitrogen source, various mineral salts and if necessary growth factors (purified amino acids, vitamins, purines and pyrimidines). Various tissue culture media, including defined culture media, are commercially available, for example, any one or a combination of the following cell culture media can be used: RPMI-1640 Medium, Medium 199, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others.

In some exemplary embodiments, the method of producing a protein can be a fed-batch method.

As used herein, the term "fed-batch method," refers to a method by which a fed batch cell culture can be supplied with additional nutrients. For example, a method may comprise adding supplemental media according to a determined feeding schedule within a given time period. The "fed batch cell culture" as used herein, refer to a cell culture wherein the cells and culture medium are supplied to the culturing vessel initially and additional culture nutrients are fed, continuously or in discrete increments, to the culture during growing, with or without periodic cell and/or product harvest before termination of culture.

It is understood that the present invention is not limited to any of the aforementioned eukaryotic cells, protein, basal medium, feed medium, cell-culture medium, cell-culture production medium, method of propagating cells, method of expressing a protein, method of harvesting a protein, method of introducing into a cell a nucleic acid comprising a sequence encoding a protein and time period of adding or supplementing components in the medium and that any suitable media can be selected by any suitable means.

As used herein, the terms "include," "includes," and "including," are meant to be non-limiting and are understood to mean "comprise," "comprises," and "comprising," respectively.

In some exemplary embodiments, the disclosure provides a cell culture medium for eukaryotic cells.

In some exemplary embodiments, the disclosure provides a method for producing a protein.

In some exemplary embodiments, the disclosure provides a method for culturing eukaryotic cells for increasing production of a protein.

In some exemplary embodiments, the cell culture medium can comprise 5-methylthioadenosine in a concentration of at least about 0.05 nM, at least about 1 nM, at least about 2 nM, at least about 3 nM, at least about 4 nM, at least about 5 nM, at least about 6 nM, at least about 7 nM, at least about 8 nM, at least about 9 nM, at least about 10 nM, at least about 15 nM, at least about 20 nM, at least about 25 nM, at least about 30 nM, at least about 35 nM, at least about 40 nM, at least about 45 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 105 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 195 nM, at least about 200 nM, about 205 nM, at least about 210 nM, at least about 215 nM, at least about 220 nM, at least about 225 nM, at least about 230 nM, at least about 235 nM, at least about 240 nM, at least about 245 nM, at least about 250 nM, at least about 255 nM, at least about 260 nM, at least about 265 nM, at least about 270 nM, at least about 275 nM, at least about 280 nM, at least about 295 nM, or at least about 300 nM.

In some exemplary embodiments, the cell culture medium can comprise 5-nicotinamide in a concentration of at least about 0.05 nM, at least about 1 nM, at least about 2 nM, at least about 3 nM, at least about 4 nM, at least about 5 nM, at least about 6 nM, at least about 7 nM, at least about 8 nM, at least about 9 nM, at least about 10 nM, at least about 15 nM, at least about 20 nM, at least about 25 nM, at least about 30 nM, at least about 35 nM, at least about 40 nM, at least about 45 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 105 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 195 nM, at least about 200 nM, about 205 nM, at least about 210 nM, at least about 215 nM, at least about 220 nM, at least about 225 nM, at least about 230 nM, at least about 235 nM, at least about 240 nM, at least about 245 nM, at least about 250 nM, at least about 255 nM, at least about 260 nM, at least about 265 nM, at least about 270 nM, at least about 275 nM, at least about 280 nM, at least about 295 nM, at least about 300 nM, at least about 305 nM, at least about 310 nM, at least about 315 nM, at least about 320 nM, at least about 325 nM, at least about 330 nM, at least about 335 nM, at least about 340 nM, at least about 345 nM, at least about 350 nM, at least about 355 nM, at least about 360 nM, at least about 365 nM, at least about 370 nM, at least about 375 nM, at least about 380 nM, at least about 395 nM, at least about 400 nM, about 405 nM, at least about 410 nM, at least about 515 nM, at least about 420 nM, at least about 425 nM, at least about 430 nM, at least about 435 nM, at least about 440 nM, at least about 445 nM, at least about 450 nM, at least about 455 nM, at least about 460 nM, at least about 465 nM, at least about 470 nM, at least about 475 nM, at least about 480 nM, at least about 495 nM, at least about 500 nM, at least about 510 nM, at least about 520 nM, at least about 530 nM, at least about 540 nM, at least about 550 nM, at least about 560 nM, at least about 570 nM, at least about 580 nM, at least about 590 nM, at least about 600 nM, at least about 610 nM, at least about 620 nM, at least about 630 nM, at least about 640 nM, at least about 650 nM, at least about 660 nM, at least about 670 nM, at least about 680 nM, at least about 690 nM, at least about 700 nM, at least about 710 nM, at least about 720 nM, at least about 730 nM, at least about 740 nM, at least about 750 nM, at least about 760 nM, at least about 770 nM, at least about 780 nM, at least about 790 nM, at least about 800 nM, at least about 810 nM, at least about 820 nM, at least about 830 nM, at least about 840 nM, at least about 850 nM, at least about 860 nM, at least about 870 nM, at least about 880 nM, at least about 890 nM, at least about 900 nM, at least about 910 nM, at least about 920 nM, at least about 930 nM, at least about 940 nM, at least about 950 nM, at least about 960 nM, at least about 970 nM, at least about 980 nM, at least about 990 nM, at least about 1000 nM, at least about 1050 nM, least about 1100 nM, at least about 1150 nM, at least about 1200 nM, at least about 1250 nM, least about 1300 nM, at least about 1350 nM, at least about 1400 nM, at least about 1450 nM, least about 1500 nM, at least about 1550 nM, at least about 1600 nM, at least about 1650 nM, least about 1700 nM, at least about 1750 nM, at least about 1800 nM, at least about 1850 nM, at least about 1900 nM, at least about 1950 nM, least about 2000 nM, at least about 2050 nM, least about 2100 nM, at least about 2150 nM, at least about 2200 nM, at least about 2250 nM, least about 2300 nM, at least about 2350 nM, at least about 2400 nM, at least about 2450 nM, at least about 2500 nM, at least about 2550 nM, at least about 2600 nM, at least about 2650 nM, least about 2700 nM, at least about 2750 nM, at least about 2800 nM, at least about 2850 nM, at least about 2900 nM, at least about 2950 nM, or least about 3000 nM.

In some exemplary embodiments, the cell culture medium can have a pH of about 6.5 to about 8.0. In some specific exemplary embodiments, the cell culture medium can have a pH of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

In some exemplary embodiments, the eukaryotic cells are grown at a temperature of about 25° C. to about 40° C. In some specific exemplary embodiments the eukaryotic cells are grown at a temperature of about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.

In some exemplary embodiments, the cell culture medium can comprise at least about 10 nM 5-methylthioadenosine, wherein a titer of a protein produced in the cell culture medium can be at least about 2% greater than another cell culture medium that does not have at least about 10 nM 5-methylthioadenosine. In one aspect, the cell culture medium can comprise at least about 20 nM 5-methylthioadenosine, at least about 30 nM 5-methylthioadenosine, at least about 40 nM 5-methylthioadenosine, at least about 50 nM 5-methylthioadenosine, at least about 60 nM 5-methylthioadenosine, at least about 70 nM 5-methylthioadenosine, at least about 80 nM 5-methylthioadenosine, at least about 90 nM 5-methylthioadenosine, at least about 100 nM 5-methylthioadenosine, at least about 110 nM 5-methylthioadenosine at least about 120 nM 5-methylthioadenosine, at least about 130 nM 5-methylthioadenosine, at least about 140 nM 5-methylthioadenosine, at least about 150 nM 5-methylthioadenosine, at least about 160 nM 5-methylthioadenosine, at least about 170 nM 5-methylthioadenosine, at least about 180 nM 5-methylthioadenosine, at least about 190 nM 5-methylthioadenosine or at least about 200 nM 5-methylthioadenosine. In one aspect, the titer of a protein produced in the cell culture medium can be greater by at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30%.

In some exemplary embodiments, the cell culture medium can comprise at least about 50 nM nicotinamide, wherein a titer of a protein produced in the cell culture medium can be at least about 2% greater than another cell culture medium that does not have at least about 50 nM nicotinamide. In one aspect, the cell culture medium can comprise at least about 50 nM nicotinamide, at least about 100 nM nicotinamide, at least about 150 nM nicotinamide, at least about 200 nM nicotinamide, at least about 250 nM nicotinamide, at least about 300 nM nicotinamide, at least about 350 nM nicotinamide, at least about 400 nM nicotinamide, at least about 450 nM nicotinamide, at least about 500 nM nicotinamide at least about 550 nM nicotinamide, at least about 600 nM nicotinamide, at least about 650 nM nicotinamide, at least about 700 nM nicotinamide, at least about 750 nM nicotinamide, at least about 800 nM nicotinamide, at least about 850 nM nicotinamide, at least about 900 nM nicotinamide or at least about 1000 nM nicotinamide. In one aspect, the titer of a protein produced in the cell culture medium can be greater by at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30%.

In some exemplary embodiments, the cell culture medium can comprise feeding the eukaryotic cells using an enriched media having 5-methylthioadenosine at a concentration of at least about 0.05 nM, at least about 1 nM, at least about 2 nM, at least about 3 nM, at least about 4 nM, at least about 5 nM, at least about 6 nM, at least about 7 nM, at least about 8 nM, at least about 9 nM, at least about 10 nM, at least about 11 nM, at least about 12 nM, at least about 13 nM, at least about 14 nM, at least about 15 nM, at least about 20 nM, at least about 25 nM, at least about 30 nM, at least about 35 nM, at least about 40 nM, or at least about 50 nM.

In some exemplary embodiments, the cell culture medium can comprise feeding the eukaryotic cells using an enriched media having nicotinamide at a concentration of at least about 1 nM, at least about 2 nM, at least about 3 nM, at least about 4 nM, at least about 5 nM, at least about 6 nM, at least about 7 nM, at least about 8 nM, at least about 9 nM, at least about 10 nM, at least about 15 nM, at least about 20 nM, at least about 25 nM, at least about 30 nM, at least about 35 nM, at least about 40 nM, at least about 50 nM, at least about 55 nM, at least about 60 nM, at least about 65 nM, at least about 70 nM, at least about 75 nM, at least about 80 nM, at least about 85 nM, at least about 90 nM, at least about 95 nM, at least about 100 nM, at least about 105 nM, at least about 110 nM, at least about 115 nM, at least about 120 nM, at least about 125 nM, at least about 130 nM, at least about 135 nM, at least about 140 nM, at least about 145 nM, at least about 150 nM, at least about 155 nM, at least about 160 nM, at least about 165 nM, at least about 170 nM, at least about 175 nM, at least about 180 nM, at least about 195 nM, or at least about 200 nM.

In some exemplary embodiments, the cell culture medium can comprise feeding the eukaryotic cells using an enriched media having 5-methylthioadenosine at a concentration of at least about 1 nM, wherein a titer of a protein produced in the cell culture medium can be at least about 2% greater than another cell culture medium that does not have at least about 10 nM 5-methylthioadenosine. In one aspect, the enriched media can have at least about 2 nM 5-methylthioadenosine, at least about 3 nM 5-methylthioadenosine, at least about 4 nM 5-methylthioadenosine, at least about 5 nM 5-methylthioadenosine, at least about 6 nM 5-methylthioadenosine, at least about 7 nM 5-methylthioadenosine, at least about 8 nM 5-methylthioadenosine, at least about 9 nM 5-methylthioadenosine, at least about 10 nM 5-methylthioadenosine, at least about 11 nM 5-methylthioadenosine at least about 12 nM 5-methylthioadenosine, at least about 13 nM 5-methylthioadenosine, at least about 14 nM 5-methylthioadenosine, at least about 15 nM 5-methylthioadenosine, at least about 16 nM 5-methylthioadenosine, at least about 17 nM 5-methylthioadenosine, at least about 18 nM 5-methylthioadenosine, at least about 19 nM 5-methylthioadenosine or at least about 20 nM 5-methylthioadenosine. In one aspect, the titer of a protein produced in the cell culture medium can be greater by at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30%.

In some exemplary embodiments, the cell culture medium can comprise feeding the eukaryotic cells using an enriched media having nicotinamide at a concentration of at least about 5 nM, wherein a titer of a protein produced in the cell culture medium can be greater by at least about 2% than another cell culture medium that does not have at least about 50 nM nicotinamide. In one aspect, the cell culture medium can comprise at least about 5 nM nicotinamide, at least about 10 nM nicotinamide, at least about 15 nM nicotinamide, at least about 20 nM nicotinamide, at least about 25 nM nicotinamide, at least about 30 nM nicotinamide, at least about 35 nM nicotinamide, at least about 400 nM nicotinamide, at least about 45 nM nicotinamide, at least about 50 nM nicotinamide at least about 55 nM nicotinamide, at least about 60 nM nicotinamide, at least about 65 nM nicotinamide, at least about 70 nM nicotinamide, at least about 75 nM nicotinamide, at least about 80 nM nicotinamide, at least about 85 nM nicotinamide, at least about 90 nM nicotinamide, at least about 95 nM nicotinamide or at least about 100 nM nicotinamide. In one aspect, the titer of a protein produced in the cell culture medium can be greater by at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30%.

In some exemplary embodiments, the protein can be a naturally occurring protein.

In some exemplary embodiments, the protein can be a recombinant protein.

In some exemplary embodiments, the protein can be a bio-therapeutic protein.

In some exemplary embodiments, the protein can be a recombinant protein, wherein the recombinant protein can be a trap protein, a chimeric receptor Fc-fusion binding molecule, a chimeric protein, an antibody, monoclonal antibody, a polyclonal antibody, a human antibody, a bispecific antibody, an antibody fragment, a nanobody, a recombinant antibody chimera, a cytokine, a chemokine, or a peptide hormone.

In some exemplary embodiments, the protein can comprise modifications, adducts, and other covalently linked moieties.

In some exemplary embodiments, the protein can comprise a post-translational modification.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

EXAMPLES

To study the contents of a cell culture medium and its effect on the production of a protein, cell culture comprising soy hydrolysate was selected for generating a VEGFR binding protein 1.

Example 1

Soy hydrolysate content analysis was performed using nine different lots obtained from three distinct shipments— 1, 2 and 3. The samples from these three distinct shipments were sent to Metabolon (Durham, N.C., USA). The soy hydrolysate content analysis was conducted at Metabolon using liquid chromatography-mass spectrometer. Over three hundred components in the soy hydrolysate were measured. Only the results scaled to median were provided.

For studying the effect of biochemicals on the titer of VEGFR (Vascular Endothelial Growth Factor Receptor) binding protein 1, an orthogonal partial least squares (OPLS) model was used for multivariate analysis (MVA). Seventy soy hydrolysates lot were included in the study.

The dependence between the components and titer was evaluated by studying the correlation and covariance. A positive dependence suggests an increase in titer with increase in the biochemical and a negative dependence suggests a decrease in titer with increase in the biochemical. For the final titer evaluation for a principal component, the values for $R^2X$, $R^2Y$ and $Q^2$ were found to be 0.315, 0.672, and 0.493, respectively. The components that showed positive dependence are shown in Table 1 and the components that showed negative dependence are shown in Table 2.

TABLE 1

| Positive dependence |
| --- |
| Nicotinamide |
| Lactate |
| phenyllactate (PLA) |
| 5-methylthioadenosine (MTA) |
| Indolelacate |
| Succinate |
| alpha-hydroxyisocaproate |
| 3-(4-hydroxyphenyl)lactate (HPLA) |
| alpha-hydroxyisovalerate |
| 2-hydroxy-3-methylvalerate |

TABLE 2

| Negative dependence |
| --- |
| Nicotinate |
| Sucrose |
| Uracil |
| Phenylalanine |
| Valyleucine |
| Maltose |
| digalactosylglycerol |
| pantothenate (Vitamin B5) |
| Xanthine |
| Serine |

The MVA result normalized to unit length is shown in FIG. 1. Based on these finding from example 2, nicotinamide and 5-methythioadenosine were selected as positive markers for further analysis.

Example 2

The impact of 5-methythioadenosine on production of a recombinant protein (VEGFR binding protein 1) was studied by investigating the protein titer (g/L) at different concentrations of 5-methythioadenosine present in the cell culture medium.

An enriched medium (soy hydrolysate) comprising 5-methythioadenosine was added to the cell culture medium. FIG. 2 shows the correlation between the concentration of 5-methylthioadenosine present in the soy hydrolysate added to the cell culture medium with the titer of VEGFR binding protein 1.

As seen in FIG. 2, the regression line relating to the variables (N=70) extrapolated suggests that titer varied linearly to the concentration of 5-methythioadenosine in the soy hydrolysate added to the cell culture medium, suggesting that higher titer can be obtained on increasing 5-methythioadenosine concentration in the cell culture medium.

Example 3

Based on the correlation data obtained from studying the effect of 5-methythioadenosine concentrations in the enriched medium (soy hydrolysate) supplemented to the cell culture medium (Example 2, FIG. 2), an estimation as to the optimum concentration of 5-MTA in a cell culture was made. FIG. 3 shows the regression line relating to the variables (N=70) extrapolated suggests that titer can vary linearly to the concentration of 5-methythioadenosine in the cell culture medium showing that higher titer can be obtained on increasing 5-methythioadenosine concentration in the cell culture medium.

Example 4

The impact of nicotinamide on a recombinant protein (VEGFR binding protein 1) titer was also studied by investigating the protein titer (g/L) at different concentrations of nicotinamide present in the cell culture medium.

An enriched medium (soy hydrolysate) comprising nicotinamide was added to the cell culture medium at varying concentrations. FIG. 4 shows the correlation between the concentration of nicotinamide present in the soy hydrolysate added to the cell culture medium with the titer of VEGFR binding protein 1. As seen in FIG. 4, the regression line relating to the variables (N=70) extrapolated suggests that titer varied linearly to the concentration of nicotinamide in the soy hydrolysate, suggesting that higher titer can be obtained on increasing nicotinamide concentration in the cell culture medium.

Example 5

Based on the correlation data obtained from studying the effect of nicotinamide concentration in enriched medium (soy hydrolysate) supplemented to the cell culture medium (Example 4, FIG. 4), an estimation as to the optimum concentration of nicotinamide in a cell culture was made. FIG. 5 shows the regression line relating to the variables (N=70) extrapolated suggests that titer can vary linearly to the concentration of nicotinamide in the cell culture medium, suggesting that higher titer can be obtained on increasing nicotinamide concentration in the cell culture medium.

What is claimed is:

1. A method for culturing eukaryotic cells for increasing production of a recombinant protein, comprising the steps of:

introducing into eukaryotic cells a nucleic acid comprising a nucleotide sequence encoding a recombinant protein;

culturing eukaryotic cells in a defined cell culture medium;

supplementing the cell culture medium with nicotinamide, wherein concentration of the nicotinamide is from about 50 nM to about 1500 nM; and producing said recombinant protein in the eukaryotic cells, wherein the supplementation with nicotinamide increases a titer of the recombinant protein.

2. The method of claim 1, wherein the eukaryotic cells include at least one selected from the group consisting of: Baby Hamster Kidney cell lines, Chinese Hamster Ovary cell lines, Murine myeloma cell lines, Mouse myeloma cell lines, Human embryonic kidney cell lines, Human-retina-derived cell lines, and Amniocyte cell lines.

3. The method of claim 1, wherein the recombinant protein is secreted in the medium.

4. The method of claim 1, wherein the cell culture medium does not have a protein derived from an animal.

5. The method of claim 1, wherein the cell culture medium is a serum-free medium.

6. The method of claim 1, wherein the cell culture medium is a chemically-defined medium.

7. A method for producing a recombinant protein, comprising:
   introducing into a eukaryotic cell a nucleic acid comprising a nucleotide sequence encoding a recombinant protein;
   culturing the eukaryotic cell in a cell culture medium comprising from about 50 nM to about 1500 nM nicotinamide or from about 10 nM to about 200 nM 5-methylthioadenosine; and
   producing the recombinant protein in the eukaryotic cell.

\* \* \* \* \*